United States Patent [19]

Glover

[11] Patent Number: 5,306,233
[45] Date of Patent: Apr. 26, 1994

[54] ENDOTRACHEAL TAPE AND METHOD OF USE

[75] Inventor: David F. Glover, P.O. Box 1424, Wheat Ridge, Colo. 80034

[73] Assignee: David F. Glover, Wheat Ridge, Colo.

[21] Appl. No.: 27,675

[22] Filed: Mar. 8, 1993

[51] Int. Cl.$^5$ .............................................. A01F 13/00
[52] U.S. Cl. ..................................... 602/41; 602/903; 126/207.17
[58] Field of Search .................... 602/903, 41, 42, 52, 602/54, 58, 60, 902, 57; 128/207.17, 852; 206/391, 394, 411

[56] References Cited

U.S. PATENT DOCUMENTS 5,038,778  8/1991  Lott ................................ 126/207.17

Primary Examiner—Robert Bahr
Assistant Examiner—Beverly A. Meindl
Attorney, Agent, or Firm—David F. Glover

[57] ABSTRACT

An endotracheal tape for adhesively securing an endotracheal tube in position is disclosed. The tape consists of a single piece of 1 inch wide tape having first and second opposite ends split into two identical sections. A single short, non-stick piece is centered along the length of the tape and the tape is rolled onto two plastic tubes from each of the first and second ends. To dispense the device, the tape is unrolled slightly from the tubes to expose the short non-stick piece and the piece is placed against the back of the patient's neck. The tape is then completely unrolled and the upper halves of the split ends are affixed above the patient's nose or mouth and the lower halves of the split ends are wrapped around an endotracheal tube.

1 Claim, 1 Drawing Sheet

ENDOTRACHEAL TAPE AND METHOD OF USE

BACKGROUND OF THE INVENTION

The placement of an endotracheal tube is crucial to the bilateral ventilation of a patient's lungs. Endotracheal tape, when used in conjunction with an endotracheal tube, assures proper placement of an endotracheal tube by securing the tube to the facial and/or neck area of a patient. Thus, endotracheal tape prevents endotracheal tube slippage or inadvertent extubation (inadvertent removal of the tube delivering life sustaining medical gases).

In current practice, caregivers utilize either cloth adhesive tape or a cloth fabric material having a Velcro securing device for securement of an endotracheal tube. However, several problems arise when using either of these arrangements. First, in using the cloth tape, as the need arises, caregivers locate a roll of cloth adhesive tape, tear a strip off, lay the strip on a table top and proceed to fabricate the securing tape (the end product) by cutting or tearing the tape to suit the situation. A problem with this "on the spot" fabrication is the loss of valuable time as a result of having to locate a roll of suitable tape. Furthermore, the tape will occasionally stick to itself resulting in an additional loss of time as another strip is cut and subsequently fabricated to suit the situation. Second, in using the cloth fabric having a Velcro securing device, the fabric often becomes saturated with secretions. Furthermore, the Velcro securing device often fails to adhere in both initial application and in reapplication following repositioning. Replacement of this type of device is not cost effective since the apparatus, due to the Velcro securing device, must be specially manufactured and ordered in quantities. Finally, the packaging makes the apparatus bulky such that caregivers do not consistently carry the device and consequently, a device may not be available in the event of emergency intubation.

SUMMARY

The advantages of the instant invention include savings in time, particularly in critical situations and compactness lending easy storage and portability. Since the device is prefabricated, a caregivers can carry a device in his or her pocket whereas with previous devices, the device is either fabricated at the site or retrieved from a storage area. In addition, there is a reduced amount of slippage of the endotracheal tube in comparison with other devices. In short, the instant invention will provide caregivers including paramedics, EMT personnel in the field and the medical staffs in hospitals and nursing homes a fast and effective means of securing an endotracheal tube in both emergency and routine care situations.

DETAILED DESCRIPTION OF THE INVENTION

Figure 1:
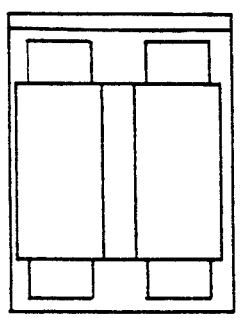
FIG. 1 is a frontal view of the instant invention in its pre-packaged form.
Figure 2:
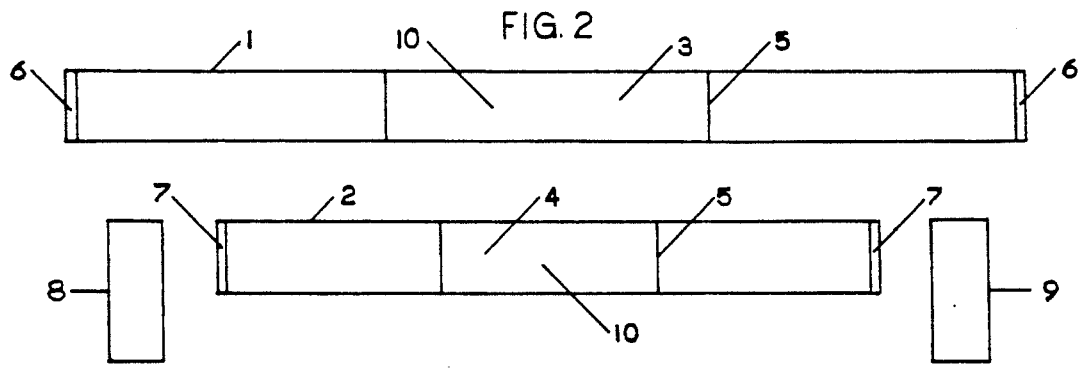
FIG. 2 is a frontal view of the two prefabricated lengths of the instant invention.
Figure 3:
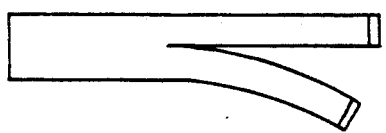
FIG. 3 is a frontal view of the split ends.

With reference to FIG. 2, the instant invention consists of a single piece of one inch wide adhesive tape prefabricated in two lengths: 76.2 cm long for adult patients 1 and 66 cm long for pediatric patients 2. In both the adult and pediatric lengths, short non-stick pieces 3 and 4 are centered along the length and attached by adhesive to the longer piece 5 thus creating a non-adhesive surface for the back of the patient's neck. Adhesive portions are disposed adjacent to and on either side of the short non-stick pieces 3 and 4. Distal ends 6 and 7 of each tape are folded and cut 0.25 inches into the overall length in aid in tearing. As shown in FIG. 3, first and second ends of each length are split into two identical sections and coated with an adhesive. The ends of an individual length of tape are rolled from opposite distal ends onto two plastic tubes 8 and 9 and placed within a suitable pre-sealed, clear plastic wrapping to form the package shown in FIG. 1.

Figure 4:
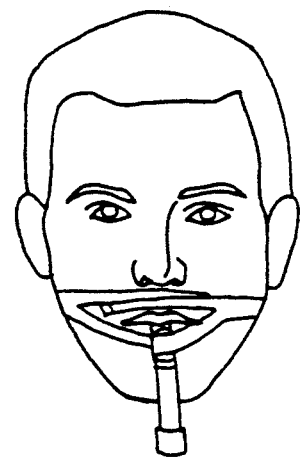
FIG. 4 is a frontal view of the instant invention in place around and endotracheal tube and secured to a patient's face.

In applying the device, the plastic wrapping is torn and the endotracheal tape is removed from the wrapping. Next, the tape is unrolled toward the first and second ends to expose the short non-stick piece. Then, the non-stick piece is placed against the back of the patient's neck and the tape is further unrolled toward the first and second ends up and across each side of the patient's face. Next, the first and second ends are torn to a desired length. The upper half of each split end is affixed above the lip or nose and the lower half of each split distal end is wrapped around an endotracheal tube as shown in FIG. 4.

I claim:

1. A method for applying an endotracheal tube tape to the face and neck of a patient comprising the steps of:
   a. providing a single piece of 1 inch wide endotracheal tape comprising: first and second opposite ends that are split into two identical sections and coated with an adhesive, a single short non-stick piece centered along the length of said tape and adhesive portions disposed adjacent to and on either side of said cloth where said tape is rolled from said first and second opposite ends onto two plastic tubes and packaged in a pre-sealed, clear plastic wrap;
   b. tearing said plastic wrap and removing said endotracheal tape;
   c. unrolling said endotracheal tape toward said first and second ends to expose said short non-stick piece;
   d. placing said cloth against the back of the patient's neck;
   e. further unrolling the endotracheal tape toward said first and second ends up and across each side of the face;
   f. tearing said first and second ends to a desired length;
   g. affixing the upper half of said split end of said first end above the lip or nose;
   h. wrapping the lower half of said split end of said first end around an endotracheal tube;
   i. repeating steps g and h with the upper and lower halves of said second end.

* * * * *